(12) United States Patent
Cheng et al.

(10) Patent No.: US 8,460,238 B2
(45) Date of Patent: Jun. 11, 2013

(54) DRUG DELIVERY CATHETER WITH SOLUBLE BALLOON COATING CONTAINING RELEASABLE MICROSPHERES AND DELIVERY METHOD

(75) Inventors: Peiwen Cheng, Santa Rosa, CA (US); Justin Peterson, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 560 days.

(21) Appl. No.: 12/728,860

(22) Filed: Mar. 22, 2010

(65) Prior Publication Data

US 2010/0249749 A1 Sep. 30, 2010

Related U.S. Application Data

(60) Provisional application No. 61/163,264, filed on Mar. 25, 2009.

(51) Int. Cl.
*A61M 31/00* (2006.01)
(52) U.S. Cl.
USPC .................................. 604/103.02; 604/103.01

(58) Field of Classification Search
USPC ................. 604/96.01, 99.01, 103.01, 103.02, 604/103.06, 103.08, 509, 915
See application file for complete search history.

(56) References Cited

U.S. PATENT DOCUMENTS

| 5,102,402 | A | | 4/1992 | Dror et al. |
| 5,681,281 | A | * | 10/1997 | Vigil et al. ............... 604/103.01 |
| 6,129,705 | A | * | 10/2000 | Grantz ...................... 604/103.02 |
| 6,537,195 | B2 | * | 3/2003 | Forman ............................ 600/3 |
| 2002/0004641 | A1 | * | 1/2002 | Bellhouse et al. ............... 604/68 |
| 2002/0082552 | A1 | * | 6/2002 | Ding et al. ............... 604/103.02 |
| 2006/0190022 | A1 | * | 8/2006 | Beyar et al. .................... 606/192 |
| 2008/0069801 | A1 | | 3/2008 | Lee et al. |
| 2008/0124400 | A1 | | 5/2008 | Liggins et al. |

* cited by examiner

Primary Examiner — Kevin C Sirmons
Assistant Examiner — Kami A Bosworth

(57) ABSTRACT

A drug delivery catheter and method for delivering microcapsules or microspheres containing a drug, pharmacological or other bioactive agent includes a balloon catheter having a coating on the balloon of a soluble biocompatible polymer containing a plurality of microcapsules or microspheres containing a drug or other agent. The balloon is porous to allow it to be inflated with a solvent fluid that passes through the porous wall of the balloon and dissolves the polymer, releasing the microspheres.

4 Claims, 3 Drawing Sheets

DRUG DELIVERY CATHETER WITH SOLUBLE BALLOON COATING CONTAINING RELEASABLE MICROSPHERES AND DELIVERY METHOD

RELATED APPLICATIONS

This application claims the benefit of U.S. Provisional Patent Application 61/163,264 filed Mar. 25, 2009.

FIELD OF THE INVENTION

This invention relates to catheters for delivering drugs, pharmacological agents and the like in microsphere form to a targeted region in a patient.

BACKGROUND

The prior art and medical practitioners have long recognized the desirability to deliver drugs or other bioactive or pharmacologically active agents directly to a specific location in the body instead of by systemic delivery. Localized delivery is particularly desirable in vascular applications, for example, to deliver drugs adapted to prevent restenosis as may occur after a procedure such as angioplasty or stent placement. For example, one such technique is described in U.S. Pat. No. 5,102,402 (Dror) in which a coating of body-affecting chemicals in the form of microcapsules are applied to the exterior of a balloon of a balloon catheter. The coating releases from the balloon when the balloon is inflated into contact with and against the vascular lumen to be treated.

SUMMARY OF THE INVENTION

The invention provides an alternate system for delivering biologically active materials in microsphere form to a specific target location within a patient, such as a particular location within the vascular system. The invention may be practiced, for example, in connection with medications intended to prevent clotting or to deliver agents adapted to prevent restenosis following an angioplasty procedure. The invention is not limited, however, to post-angioplasty applications but may be adapted for use in other appropriate circumstances. The system includes a delivery catheter having a balloon on its distal end and an inflation lumen in communication with the balloon to permit balloon inflation and deflation. The balloon is porous to allow fluid under pressure to pass through the balloon wall while also causing the balloon to inflate. The exterior of the balloon is coated with a soluble layer in which microspheres carrying the selected agent are embedded. The drugs are delivered by advancing the catheter balloon to the intended delivery site and then directing a solvent into the balloon under pressure sufficient to inflate the balloon and cause solvent to flow through the pores of the balloon into contact with the soluble polymer. As the polymer is dissolved, the microspheres are released at the target region and against the inner luminal wall of the vessel. The balloon is maintained in its inflated state for a predetermined time interval to release the microspheres while urging them against the vessel wall to be embedded in the vessel wall and in crevices and fissures that may have existed before or created during angioplasty. The microspheres preferably are formed from a biodegradable material (e.g., polylactic acid (PLA), polyglycolic acid (PGA), copoly lactic acid/glycolic acid (PLGA) and their copolymers) selected to degrade over time to provide a sustained release of the contained agent.

In another embodiment, the catheter shaft includes two fluid lumens, both of which are in communication with the interior of the balloon. One lumen is adapted to inflate the balloon with a fluid that does not dissolve the coating on the exterior of the balloon. With this embodiment, the catheter may be maintained in a selected position by inflating the balloon with a non-solvent fluid and, when it is desired to release the bioactive agent, a solvent may be forced into the balloon without deflating the balloon.

A rupturable membrane may isolate the second lumen from the interior of the balloon until the clinician has decided to apply the solvent, at which time it is applied under pressure sufficient to rupture the membrane. The membrane may be in the form of an internal second balloon or may be in the form of an aperture covered with the rupturable weakened membrane.

DESCRIPTION OF THE DRAWINGS

The foregoing and other features and advantages of the invention will be apparent from the following description of the invention as illustrated in the accompanying drawings. The accompanying drawings, which are incorporated herein and form a part of the specification, further serve to explain the principles of the invention and to enable a person skilled in the pertinent art to make and use the invention. The drawings are not to scale.

DESCRIPTION OF THE ILLUSTRATIVE EMBODIMENTS

Specific embodiments of the present invention are now described with reference to the figures, wherein like reference numbers indicate identical or functionally similar elements. The terms "distal" and "proximal" are used in the following description with respect to a position or direction relative to the treating clinician. "Distal" or "distally" are a position distant from or in a direction away from the clinician. "Proximal" and "proximally" are a position near or in a direction toward the clinician.

The following detailed description is merely exemplary in nature and is not intended to limit the invention or the application and uses of the invention. Furthermore, there is no intention to be bound by any expressed or implied theory presented in the preceding technical field, background, brief summary or the following detailed description.

Figure 1:
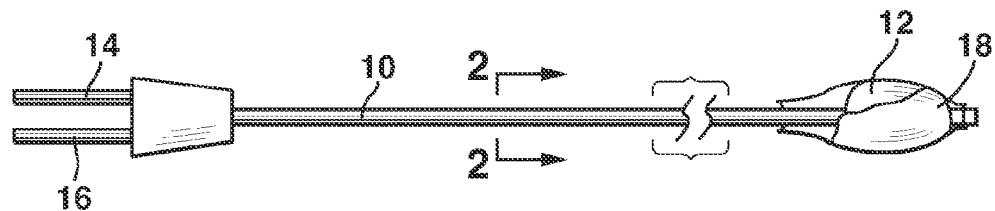
FIG. 1 is a diagrammatic, fragmented illustration of an embodiment of the delivery catheter with the balloon inflated and with part of the balloon and coating broken away.
Figure 2:
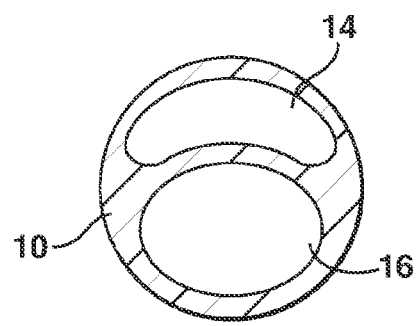
FIG. 2 is a diagrammatic sectional illustration of the catheter shaft as seen along the line 2-2 of FIG. 1.

As shown in FIG. 1, the catheter includes a shaft 10 having proximal and distal ends and a balloon 12 mounted adjacent the distal end. Shaft 10 has at least one lumen 14 for inflation of the balloon 12 and typically will have a second lumen 16 adapted to receive a guidewire for guiding the catheter to the intended site within the patient's vasculature. Shaft 10 may be formed from any of a variety of polymers used in the art, and known to those skilled in the art for such purpose. For example, the shaft may be formed from polyethylene, polyamide, or polyethylene block amide copolymer. As shown in FIG. 2, shaft 10 may be made of a multi-lumen extruded thermoplastic polymer. Alternatively, the shaft may be of coaxial, i.e. tube-within-a-tube construction, as illustrated in other embodiments described below.

Similarly, balloon 12 may be formed from a variety of polymers from which catheter balloons are made such as polyamide, polyethylene, polyethylene terephthalate, or polyethylene block amide copolymer, among others. The degree of radial expansion of the balloon in response to inflation pressure, a property known as compliance, may be varied to suit the particular intended application.

Figure 3:
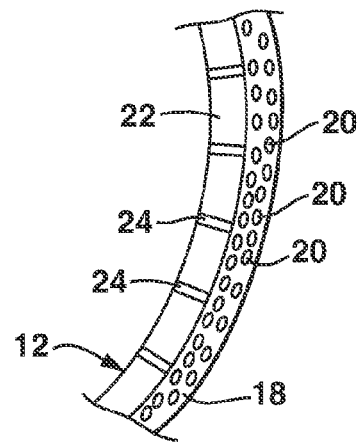
FIG. 3 is an enlarged diagrammatic sectional illustration of a portion of the balloon wall illustrating pores in the wall and the outer coating with embedded microspheres.

As shown diagrammatically in FIG. 3, the external surface of the balloon is coated with a biocompatible polymeric layer 18 that is formulated to contain a plurality of microcapsules or microspheres 20 containing a selected drug, pharmacological agent or other bioactive agent as may be desired for therapeutic, diagnostic or other purposes. Layer 18 is formed from a soluble polymer adapted to be dissolved when exposed to a selected solvent fluid so as to release the microspheres 20. The wall 22 of balloon 12 is porous, as suggested diagrammatically by pores 24 to enable a solvent to flow through balloon wall 22 into contact with polymeric layer 18 to dissolve layer 18. Layer 18 covers and blocks pores 24 until it has been exposed to the solvent, under pressure, and the polymer matrix has been dissolved.

By way of example, the soluble polymer comprising layer 18 may be a natural polymer such as a starch or a hydrogel. The solvent for dissolving layer 18 may be, for example, sterile phosphate buffered saline, deionized water, or a low concentration ethanol. It should be understood that various combinations of polymers and solvents may be used as will be understood by those skilled in the art.

Figure 4A:
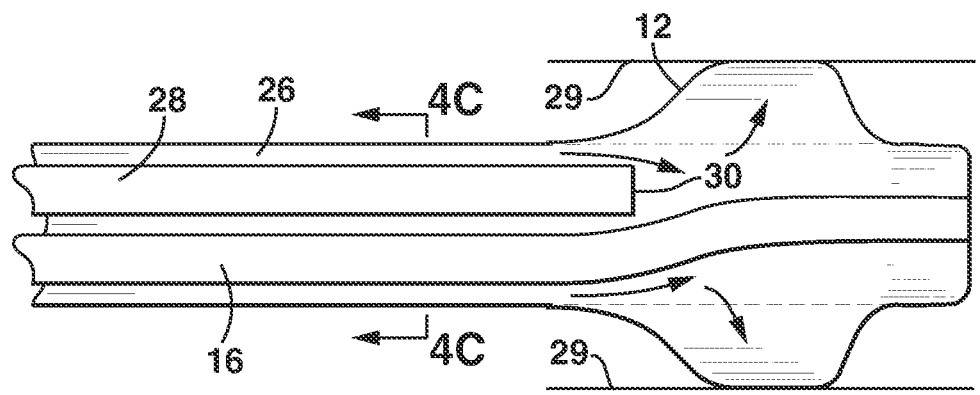
FIG. 4A is a diagrammatic longitudinal sectional illustration of a second embodiment of the invention.

FIG. 4A illustrates another embodiment of the invention in which the catheter shaft has two fluid carrying lumens 26, 28, both of which are in communication with the interior of the balloon 12. A third guidewire lumen 16 also may be provided. In this example, lumens 16 and 28 are defined by elongate tubular components that extend through a third elongate tube defining lumen 26. Balloon 12 is coated on its external surface with the microsphere-embedded matrix layer 18 as described above in connection with the embodiment of FIG. 1. In this embodiment, two inflation fluids are applied sequentially through their respective lumens 26, 28 into the balloon. The first fluid, which is selected so as not to dissolve layer 18, is applied through first lumen 26 to inflate balloon 12 against the wall 29 of the vessel. A solvent fluid then may be applied under pressure through second lumen 28. The second lumen 28 may be obstructed by a frangible cap or membrane 30 to prevent the solvent from being applied until the clinician has determined that the balloon is properly positioned and inflated and in readiness to release the microspheres against the vessel wall. Membrane 30 is selected to rupture under a predetermined pressure as controlled by the clinician. The membrane may be formed from any of a variety of polymeric materials or may be formed from the material that defines the second lumen, as by forming the lumen to be closed and weakening the closing portion with break lines or laser etching to rupture at a predetermined pressure.

Figure 4B:
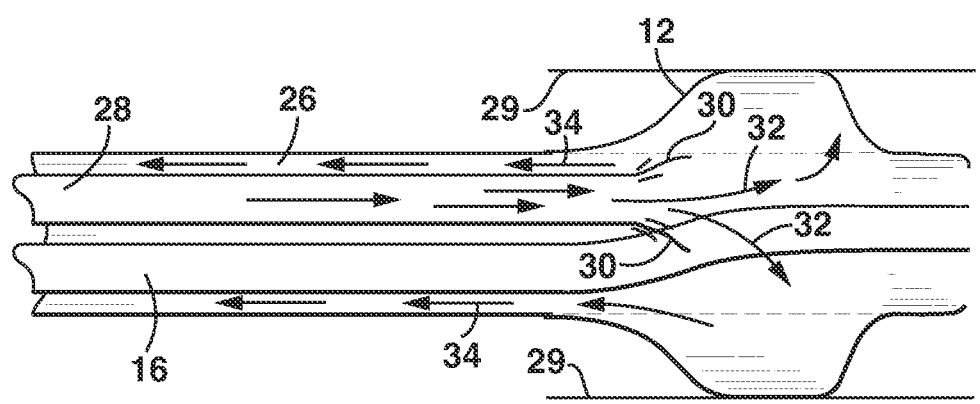
FIG. 4B is a diagrammatic illustration of the embodiment of FIG. 4A in which a membrane of a second lumen has ruptured to allow solvent liquid to flow into the balloon.

When membrane 30 ruptures, the solvent liquid flows from lumen 28 into the interior of balloon (arrows 32, FIG. 4B) and the initial inflation liquid may be flushed from the interior of balloon 12 by exiting through the first lumen 26 as suggested by arrows 34. Continued application of pressure to the solvent liquid will maintain the balloon in its inflated state against the vessel wall and will dissolve layer 18 and release the microspheres 20 as described above in connection with the embodiment of FIG. 1.

Figure 4C:
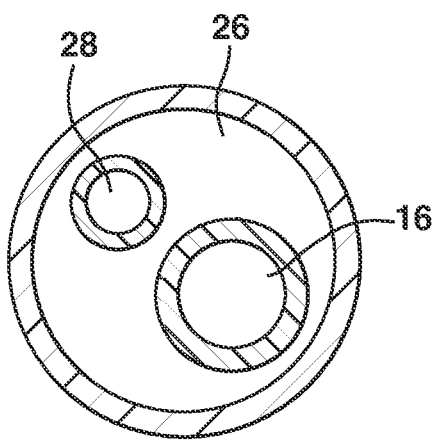
FIG. 4C is a diagrammatic sectional illustration of the catheter shaft of the embodiment of 4A as seen along the line 4c-4c of FIG. 4A.
Figure 5:
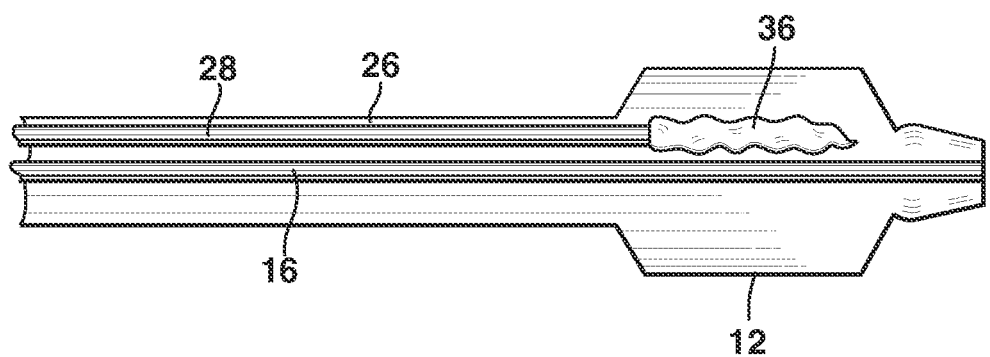
FIG. 5 is a diagrammatic illustration, in section, of a third embodiment of the invention.

FIG. 5 illustrates a modified embodiment of the arrangement of FIG. 4 in which the rupturable membrane may be the form of an inner balloon-like element or bag 36 contained within the outer porous balloon 12. Inner bag 36 serves as a rupturable membrane to prevent application of the solvent until the clinician has decided to do so. At that time, pressure applied through the second lumen 28 with a solvent liquid will rupture bag 36 to cause the non-solvent inflation liquid in balloon 12 to be replaced with the solvent liquid, as described above in connection with the embodiment of FIG. 4.

Pre-inflation of the balloon with a non-solvent is desirable in those instances where the particular solvent-polymer combination might result in rapid, premature dissolution of the coating and premature release of the microspheres before they had sufficient opportunity to become embedded in the vascular wall. Where the solvent-polymer combination is selected to allow full balloon inflation before microsphere release, a single-lumen catheter may be used with the solvent functioning to inflate the balloon as well as to dissolve the coating.

In practicing the invention, the catheter is advanced until the ballon is in position at the treatment site. The balloon then is inflated against the lumen wall. If inflated with solvent, pressure is maintained to cause the solvent to flow through the porous balloon wall to dissolve the polymer matrix. The balloon is maintained in its inflated state for a predetermined time interval sufficient to release the microspheres against the vessel walls. After the microspheres are released, the balloon may be deflated and the catheter may be removed. If pre-inflated with a non solvent, the clinician, after determining that the balloon has been inflated properly and fully, then applies pressure to solvent in the second lumen, enabling the non-solvent to be flushed out via the first lumen. The balloon then is maintained in its inflated state with solvent to effect release and placement of the microspheres.

While various embodiments according to the present invention have been described above, it should be understood that they have been presented by way of illustration and example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

We claim:
1. A delivery catheter for delivering pharmacological, chemical, or bioactive agents at a selected location within a patient's body comprising:
    a shaft having proximal and distal ends and a first lumen extending through the shaft;
    a balloon mounted about a distal region of the shaft, the balloon being expandable and having a porous wall adapted to enable fluid directed under pressure through the first lumen into an interior of the balloon to be forced through the porous balloon wall; and a coating covering an external surface of the balloon and blocking pores of the porous wall therein, the coating comprising a matrix formed from a biocompatible polymer soluble in a selected biocompatible fluid solvent and a plurality of microspheres carrying a selected agent;

whereby the balloon is adapted to be inflated with the selected fluid solvent to dissolve the coating polymer and thereby release the microspheres from the matrix.

2. The delivery catheter as defined in claim 1 further comprising the shaft having a second lumen extending therethrough and being adapted to receive a guidewire.

3. The catheter as defined in claim 1 further comprising:

the shaft having the first lumen and a second lumen fluidly communicating the interior of the balloon with the proximal end of the shaft, the second lumen having a frangible membrane adapted to temporarily isolate the second lumen from communication with the interior of the balloon until the membrane is ruptured under influence of a fluid pressure within the second lumen;

whereby the balloon is adapted to be inflated by a nonsolvent fluid delivered through the first lumen, the polymer of the coating being insoluble in the nonsolvent fluid; and whereby the polymer of the coating is adapted to be dissolved by applying the selected fluid solvent through the second lumen after the non-solvent fluid has inflated the balloon.

4. The catheter as defined in claim 3 wherein the frangible membrane comprises a bag disposed within the balloon and is in fluid communication with the second lumen.

\* \* \* \* \*